United States Patent
Mammone et al.

(10) Patent No.: US 6,514,506 B1
(45) Date of Patent: Feb. 4, 2003

(54) WHITENING COMPOSITIONS CONTAINING ASCOMYCETE DERIVED ENZYME

(75) Inventors: Thomas Mammone, Farmingdale, NY (US); Steven F. Schnittger, Huntington Station, NY (US); Kenneth D. Marenus, Dix Hills, NY (US); Daniel H. Maes, Huntington, NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/783,229

(22) Filed: Feb. 14, 2001

(51) Int. Cl.$^7$ .......................... A61K 6/00; A61K 31/74; A61K 38/43; A61K 9/00
(52) U.S. Cl. ................. 424/401; 424/78.02; 424/78.03; 424/94.1; 424/400
(58) Field of Search ................................. 424/400, 401, 424/62, 94.1, 78.02, 274.1, 93.1, 93.5; 514/844

(56) References Cited

U.S. PATENT DOCUMENTS

| 5,578,296 A | | 11/1996 | Kashino et al. |
| 5,627,157 A | * | 5/1997 | Hijiya et al. .................. 514/25 |
| 5,643,587 A | * | 7/1997 | Scancarella et al. ........ 424/401 |

FOREIGN PATENT DOCUMENTS

| EP | 1 004 289 | | 5/2000 |
| FR | 2713483 | * | 6/1995 |
| JP | 6269278 | | 9/1994 |
| JP | 07010734 | * | 1/1995 |
| JP | 8119843 | | 5/1996 |
| JP | 409124438 | * | 5/1997 |
| WO | 9915148 | * | 4/1999 |

OTHER PUBLICATIONS

Luther, J. P., and Lipke, H., "Degradation of Melanin by *Aspergillus fumigatus*", Applied and Environmental Microbiology, vol. 40, No. 1, Jul. 1980, pp. 145–155.

Zeise, L., et al., Eds, "Melanin: Its Role in Human Photoprotection", chapter "Photophysics and Photochemistry of Melanin", Chedekel, M. R., Title page, pp. 11–22 from A Melanin Symposium held on Mar. 11 and 12, 1994 in Washington, D.C., Valdenmar Publishing Company, 1995.

Liu, Y–T, et al., "Isolation of a Melanolytic Fungus and its Hydrolytic Activity on Melanin", Mycologia, 87(5), pp. 651–654 (1995).

Eds. Brakhage, A. A., et al., "*Aspergillus fumigatus*; Biology, Clinical Aspects and Molecular Approaches to Pathogenicity", Title page, pp. 1–215, Karger (1999).

* cited by examiner

Primary Examiner—Jose' G. Dees
Assistant Examiner—Sharmila S. Gollamudi
(74) Attorney, Agent, or Firm—Dorene M. Price, Esq.

(57) ABSTRACT

The present invention relates to topical whitening compositions comprising a whitening effective amount of an Ascomycete-derived melanin-degrading enzyme extract and methods of preparing the composition. The compositions provide a whitening effect which occurs by degrading melanin in the skin, yet the compositions themselves do not turn dark in color. The enzyme extract can be derived from *Aspergillus fumigatus* or from *Saccharomyces cerevisiae*, and is added to the compositions of the present invention. The compositions containing the enzyme extract are twice as effective as kojic acid in producing a whitening effect on the skin.

11 Claims, 2 Drawing Sheets

Percent Reduction in Skin Color between Day 9 and Day 14

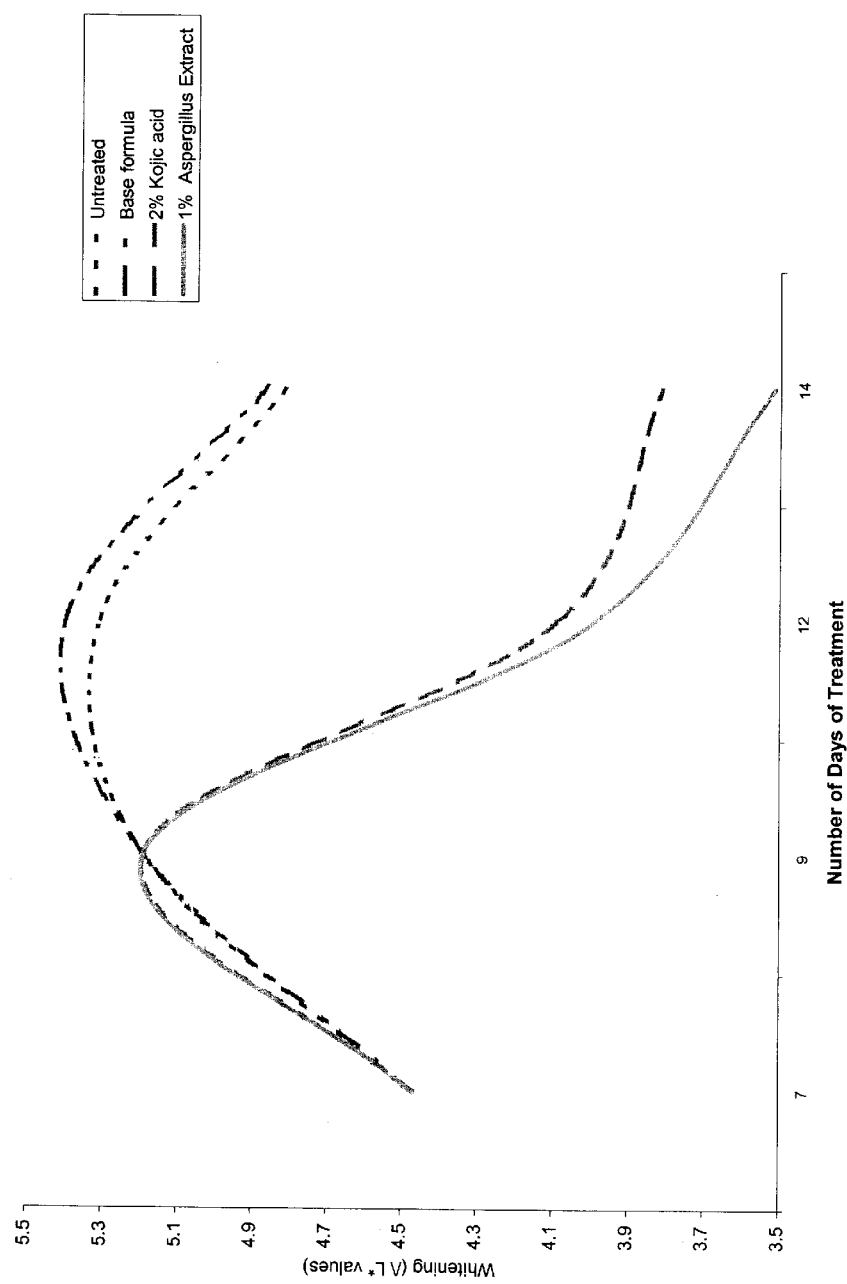
FIG. 1  Skin Whitening Effect on UV-B Induced Tan

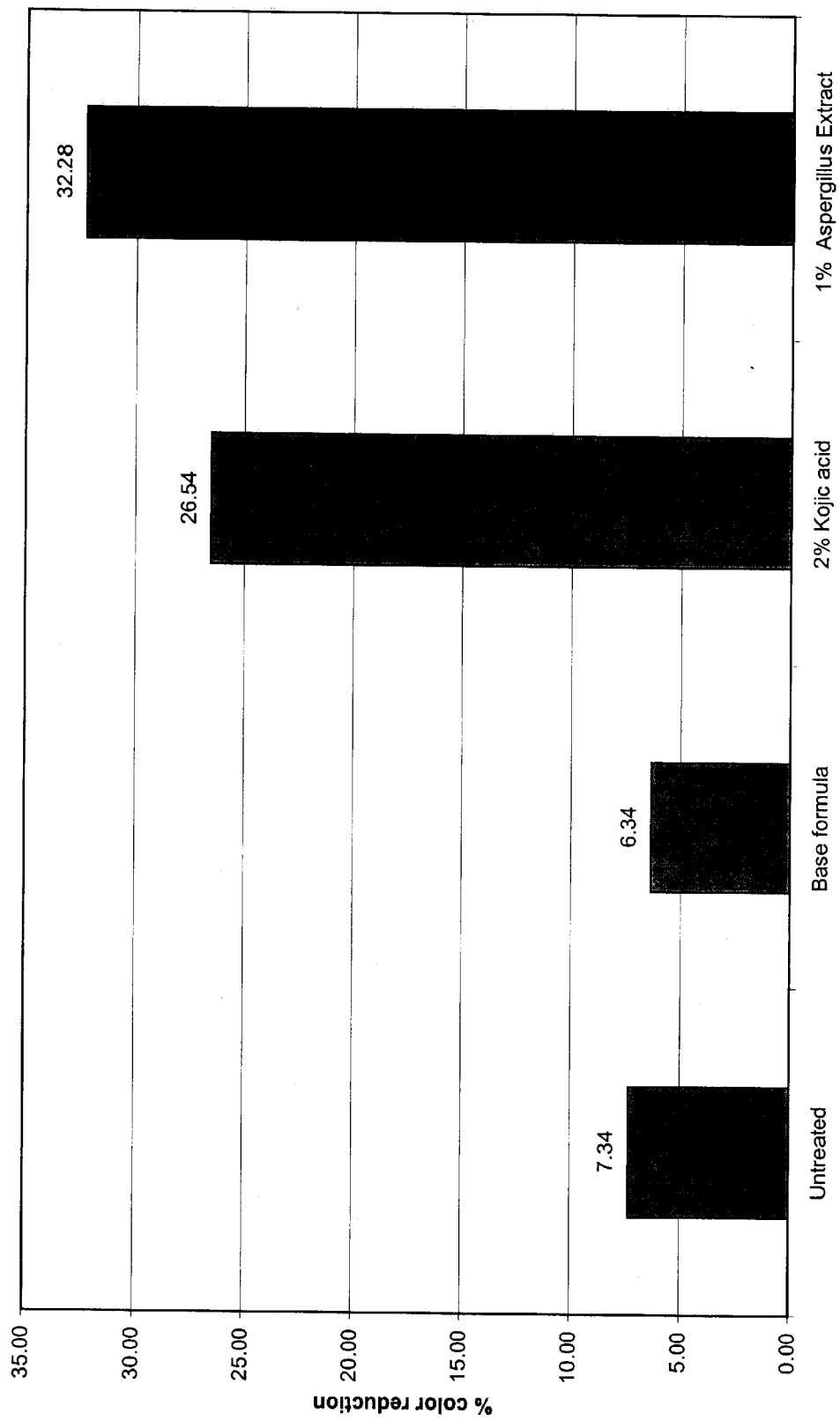
FIG. 2  Percent Reduction in Skin Color between Day 9 and Day 14

WHITENING COMPOSITIONS CONTAINING ASCOMYCETE DERIVED ENZYME

FIELD OF THE INVENTION

The invention relates to whitening compositions. More specifically, the invention relates to a whitening composition comprising an Ascomycete based enzymatic extract which degrades epidermal melanin when topically applied to the skin.

BACKGROUND OF THE INVENTION

Beauty is in the eye of the beholder. The desire to whiten the skin can be just as appealing to some as achieving a tan is to others. Thus, while a mole, beauty mark or freckled skin might be attractive to some, others may consider these dark spots on the skin to be unattractive. Dark spots are visible on the skin in areas where the production of melanin is increased. Melanin is responsible for the "color" of skin and functions to protect the skin from the harmful effects of UV light. In the skin, the production of melanin, in response to the stimulus of UV light, produces the well known tanning effect of the skin, and the natural increased production of melanin in the skin of certain ethnic groups of people produces a darker skin tone. For those who dislike the presence of dark spots on the skin or simply desire a lighter skin tone, whitening compositions are useful.

To achieve a whitening effect on the skin, various types of whitening agents are known. Hydroquinone, 4-isopropylcatechol, and hydroquinone monobenzyl ether are examples of bleaching agents. However, bleaching agents require repeat applications to the skin as the top dead cell layer of the skin sheds. When the new dead cell layer surfaces, spots darken again or reappear. In addition, bleaching agents can be irritating because of their strength, and in some instances, may cause skin conditions such as leucoderma (vitiligo), and rashing. Another method of whitening the skin is the use of whitening agents such as ascorbic acid, salicylic acid and lactic acid, which cause the top layer of dead skin cells to shed or peel off, and along with it the spots caused by increased melanin production which have migrated up to the skin surface, are also shed. This method, however, requires a long period of time, about 2 to 4 weeks, to produce a whitening effect, and also requires frequent applications.

Other known whitening agents are tyrosinase inhibitors such as, for example, kojic acid, which interfere with the production of melanin in the skin. Melanin is synthesized in melanocytes, cells that are present in the epidermal basal layer of the skin. A number of precursors lead to the production of melanin, such as tyrosine, dopa, dopa-quinone via the action of tyrosinase, and the precursor indole-5,6-dihydroquinone which is polymerized into melanin. Inhibition of any one of the precursors involved in the production of melanin in the skin thereby prevents melanin from being produced, and can achieve a depigmenting or "whitening" effect on the skin.

While the production of melanin can be inhibited, another method of whitening the skin involves the decomposition of melanin. This is described in, for example, U.S. Pat. No. 5,578,296, by using a cultured product or processed product of a species of Basidiomycetes fungus or any wood-rotting fungi having melanin decomposing potency. This method, because it breaks down melanin, allows melanin to be produced in the skin as protection against harmful UV light. However, decomposing melanin does not prevent new spots from being developed in the skin, and therefore, this method still requires repeat application like other whitening methods. Further, the Basidiomycete fungus is pre-cultured in nitrogen limited defined media. The selection of Basidiomycete fungus came after unsuccessful intensive screenings of microorganisms. In addition JP 8119843 describes a suppressant for melanin containing an extract of *Armeniacae Semen* or *Pseudocydonia sinensis Schneid.* as an active ingredient, and JP 6269278 describes a microbial strain, MEL-1 (FERM P-12991), for decoloring melanin developed on the skin.

It is also described by authors Luther and Lipke, in "Degradation of Melanin by *Aspergillus fumigatus*", Applied and Environmental Microbiology, vol. 40, no. 1, pp. 145–155 (July 1980), that a strain of *Aspergillus fumigatus*, NRRL 6463, isolated from a compost heap in Watertown, Mass., utilized synthetic tyrosine and dopa, and deproteinized hair melanins as sole sources of carbon. The *Aspergillus fumigatus* described in the study develops a black color over the course of melanin degradation. Thus, the use of *Aspergillus fumigatus* on the skin as a whitening agent is not described. Further, the structural diversity of melanin may have an effect on the identity of microorganisms which are capable of contributing to stages of melanin degradation. The composition of melanin, although it occurs widely in both marine and terrestrial animals, varies in the ratio of inolic and phenolic substituents. The chemical composition and physical properties of a certain class of melanin are highly dependent on the milieu from which it is formed. Epidermal melanin is known to have two classes of melanins, eumelanins and phaeomelanins. Eumelanin in particular includes a peptide coating. Conclusions regarding a specific melanin polymer are not a priori applicable to an entire class of melanin. "Melanin: Its Role in Human Photoprotection", Zeise, L., et al. Eds., p. 11 to 12 (Valdenmar Publishing Company 1995). The study described by Luther and Lipke used deproteinized hair melanin and synthetic precursors, and the ability of *Aspergillus fumigatus* enzyme extract for degrading melanin when topically applied to the skin has not been described. It is also not known in the prior art that a fungus derived enzyme extract can surprisingly be twice as effective in whitening the skin as a commonly used tyrosinase inhibitor.

In addition, the effect of divalent metal cations on the hydrolytic activity on melanin was found using an isolation of a melanolytic fungus of the Acrostaphylus species, a filamentous fungus belonging to the Fungi Imperfecti and reclassified as Nodulisporium. The particular strain NDMC-101 was used as disclosed by Liu, Yu-tien, in "Isolation of a Melanolytic Fungus and its Hydrolytic Activity on Melanin", Mycologia, vol. 87, no. 5, pp. 651 to 654 (1995). The Acrostaphylus species is saprophytic on wood and decaying plant materials, such as logs and stumps, dead twigs and branches of trees, and dead leaves and stems of herbacious plants. The fungal strain can utilize melanin as a nitrogen source for supporting its growth in medium containing an appropriate amount of divalent metallic ion, and therefore can degrade melanin in polluted water.

It has now been surprisingly discovered that an Ascomycete-derived enzyme extract in a cosmetic or pharmaceutical composition can be useful as a whitening agent for the skin. Accordingly, a topical whitening composition is provided by the present invention that can produce a whitening effect upon application to the skin without negative side effects and without the necessity of being combined with other types of whitening treatment.

SUMMARY OF THE INVENTION

The present invention relates to a topical cosmetic or pharmaceutical composition for application to the skin that comprises a whitening effective amount of a melanase enzyme extract derived from the Ascomycete phylum. The Ascomycete can be derived from the group of Aspergillus or Saccharomyces. In particular, the extract contains a melanin-degrading enzyme derived from a species of fungus, *Aspergillus fumigatus*, or yeast, *Saccharomyces cerevisiae*, effective in whitening the skin. Preparation of the compositions of the present invention also includes purifying the crude enzyme extract before it is added to the cosmetic or pharmaceutical composition.

In addition, the present invention includes the method of whitening the skin by topically applying the compositions containing these Ascomycete derived enzymes. The method includes extracting enzymes from *Aspergillus fumigatus* or *Saccharomyces cerevisiae*. The melanase enzyme extract is added to a cosmetic or pharmaceutical composition, and topically applied to the skin. The methods of degrading melanin production in the skin and inhibiting a UV-B induced tan by topical application of the compositions of the present invention are also included in the present invention.

BRIEF DESCRIPTION OF THE DRAWINGS

FIG. 1 is a graph illustrating the skin whitening effect on UV-B induced tan by 2% kojic acid and 1% *Aspergillus fumigatus* enzyme extract of the present invention as measured at day 7, day 9, day 12, and day 14 of a treatment regime as indicated by the change in reflectance values.

FIG. 2 is a chart illustrating the percent reduction in skin color between day 9 and day 14 on skin irradiated and treated with 2% kojic acid or 1% *Aspergillus fumigatus* enzyme extract of the present invention.

DETAILED DESCRIPTION OF THE INVENTION

In nature, fungi are regarded as a critical part of the continuous cycle of life and death of organisms. Particularly, fungi recycle usually dead organic matter into nutrients that it needs to feed itself Fungi release enzymes from hyphae, as part of their digestive system, into the surrounding environment to break down organic matter into a form of nutrients ion it can absorb. It has now been surprisingly discovered that topical application of a cosmetic or pharmaceutical composition containing a melanase enzyme derived from of large phylum, Ascomycete is effective in whitening the skin.

One particular species of the genus, Aspergillus, also known as sac fungi, is a saprotroph and can consume almost any carbonaceous substrate. The preferred Aspergillus is *Aspergillus fumigatus*. As shown in FIG. 1, the whitening effect produced with about 1% of *Aspergillus fumigatus* melanase enzyme extract is greater than the whitening effect produced using 2% of kojic acid, twice the amount of *Aspergillus fumigatus* extract. The present invention also includes the surprising discovery that an effective amount of *Aspergillus fumigatus* enzyme extract is capable of degrading epidermal melanin upon topical application to the skin.

Aspergillus conidia are ubiquitously spread in the environment. Phylogenetic analysis of 18S rDNA has supported the traditional separation between fungi with asci, the Ascomycetes, and those with basidia, the Basidiomycetes. Also, unlike the spores of the Basidiomycetes, which are produced external to the basidia and are discharged only a short distance into the space between the gills from which they randomly fall out of a cap, as for example, the cap of a mushroom, the spores of the Ascomycetes can be explosively discharged into the air as a fine white cloud. One of the most salient features of the Ascomycetes is the formation of ascospores and the release of these spores from the asci. Ascopores are usually aimed and forcibly ejected from the ascocarp. The concentration of spores in the sac of the Ascomycetes may account for the rapid growth experienced with this phylum of fungi.

The genus Aspergillus includes about 132 species and 18 variants. The *Aspergillus fumigatus* species can be found naturally in plant materials, compost, soil, and food. Various strains of *Aspergillus fumigatus* propagate in a variety of agars at temperatures ranging from about 24° C. to about 30° C. Colonies of *Aspergillus fumigatus* grow rapidly at about 45° C. on Czapek-Dox solution agar. The fungus is velvety to cottony, and white in color turning to green or gray on top. Its underside is uncolored, yellow, green or brown. *Aspergillus fumigatus* is normally silver-yellow and devoid of dark pigment unless grown on melanins or melanogens. Luther, et al. p. 146. Growth of melanase can depend on melanin. Color mutants also can occur in conidia. The conidia of *Aspergillus fumigatus* may range between rough-walled and nearly smooth, and between globose to ellipsoidal or subglobuse. The conidia are also echinulate, 1-celled and about 2.0 to 3.5 $\mu$m. Conidiophores, which bear conidia, are thin-walled, smooth, green and end in a hemispherical vesicle. *Aspergillus fumigatus* produces flask-shaped vesicles bearing phialides in a uniseriate arrangement, a single, compact column. The phialides cover the upper half of the vesicle. Its conidial heads also form a single, compact column. The hyphal wall appears two-layered. One layer is a thick translucent inner layer, and the other layer is a thin, opaque outer layer.

The melanin-degrading enzyme extract of the present invention can be prepared by first growing colonies of *Aspergillus fumigatus*, propagated and available commercially from, for example, American Type Culture Collection (ATCC), Manassas, Va. A preferred strain is NRRL 6463 available from ATCC. The fungus is available either in a point of process test tube or freeze-dried. *Aspergillus fumigatus* can be grown in malt extract agar, potato dextrose agar, YpSs agar, PYG medium or Czapek agar. Preferably, the fungus is grown in potato dextrose agar in a one-liter spinner flask, and is grown to a very high density of about $10^6$ to $10^7$ colony forming units per ml (cfu/ml). These amounts are provided as guidance and can be adjusted as necessary based on general knowledge of one skilled in the art of microbiology to achieve the desired growth rate.

The enzyme is extracted by centrifuging about 500 ml of the culture and resuspending it in about 150 mM NaCl, about 50 mM Tris buffer, and about 1 percent NP40 detergent. The resuspension is sonicated for about 30 minutes, and can then be added directly to a cosmetic or pharmaceutical formulation as a crude isolated enzyme. Preferably, the enzyme is purified by filtering it through a 0.22 $\mu$m filter. The amount of enzyme in the purified enzyme extract solution can be from about 1 to about 95 percent; preferably the enzyme is about 80 to about 95 percent of the purified solution.

The enzyme extract thus prepared is incorporated into a cosmetic or pharmaceutical formulation in a whitening effective amount. The term "whitening effective amount" as used herein means an amount of enzyme that reduces the color of the skin, as measured using a Minolta Chromameter, by about at least 25 percent, preferably by at least about 30 percent. Preferably, the whitening effective amount is from about 0.05 to about 5.00 percent by weight of the enzyme in the composition. More preferably, the enzyme is present in an amount of about 0.1 to about 2.0 percent by weight of the composition.

It has also been surprisingly discovered that a yeast-derived enzyme extract can be useful in a cosmetic or pharmaceutical formulation as a whitening agent for the skin. The particular single-celled yeast is *Saccharomyces cerevisiae* (also known as true yeast or baker's yeast, for example, strain ATCC 60219). Yeasts are characterized by solitary budding cells that undergo meiotic reproduction by ascospores. Their nucleus, like that of other eukaryotic organisms, contains a nucleolus and several chromosomes that are bound by a nuclear membrane. In yeasts, the ascospores multiply by budding or conidium formation (fission). The single-cell yeast simply becomes the ascus and usually has about 4 spores.

It is known that yeast or baker's yeast is reported to stimulate respiration of the skin. In the prior art, synergistic yeast extract is combined with peroxidase enzymes to prevent interference with peroxidase activity. However, the yeast extract in European Patent Application EP 1 004 289 is not reported as having any degradative effect on melanin in the skin. The yeast extracted for the present invention can be grown in 10% colloidal minerals (Rockland Corp., Tulsa, Okla.) in YM broth (available from Difco Labs) for several days. The yeast is sonicated, filtered and the yeast-derived enzyme is added to a cosmetic or pharmaceutical composition similar to the fungus described above.

The present invention also includes the method of whitening the skin by adding to the cosmetic or pharmaceutical composition the whitening effective amount of enzyme, either the fungus or the yeast, and topically applying the composition to the skin. The compositions of the present invention achieve a whitening effect on the skin without becoming dark colored. The compositions can be topically applied to any area of the skin intended for whitening such as, for example, the face, the legs and arms, and the torso. The whitening compositions are applied by rubbing them onto an area on the surface of the skin of about 2 mg/cm$^2$ and reapplied as necessary, as for example, on a daily basis. The whitening effect is produced in about 5 to 10 days. Its superiority as a whitening agent is observed between about 10 and 15 days. The compositions of the present invention can be chronically applied. Therefore, the whitening compositions can be prepared in any form convenient for topical application to the skin. Such forms include, but are not limited to gels, creams, colloidal dispersions, emulsions (water-in-oil or oil-in-water), suspensions, solutions, lotions, foams, mousses, sprays and the like.

The whitening compositions are formulated with a variety of cosmetically and/or pharmaceutically acceptable carriers. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. It will be apparent to the skilled artisan that the selected carrier must be compatible and relatively inert with respect to the whitening compositions. Methodology and components for formulation of compositions are well known, and can be found, for example, in Remington's Pharmaceutical Sciences, Eighteenth Edition, A. R. Gennaro, Ed., Mack Publishing Co., Easton Pa., 1990.

The whitening compositions of the present invention may be combined with one or more sunscreens. The term "sunscreen" as used herein refers to any material which is capable of protecting skin from ultraviolet radiation having a wavelength of from about 280 to about 400 nm, by effectively absorbing such radiation, and/or reflecting or scattering such radiation away from the surface of skin. Examples of sunscreens with which the compositions of the present invention can be combined in this context are titanium dioxide, zinc oxide, benzophenones, p-amino benzoic acid (PABA), octyl dimethyl PABA, amyldimethyl PABA, octyl methoxycinnamate, 2-ethoxy p-methoxycinnamate, oxybenzone, homosalate, phenyl salicylate, glyceryl p-amninobenzoate, ethyl-p-glycosylimido benzoate and the like. In a formulation, the sunscreen agent is used in the amounts normally used for that agent, and the enzyme is used in the amounts stated above.

Various other optional ingredients may be included with the whitening compositions of the present invention, these include but are not limited to fragrances, perfumes, flavorings, preservatives, emollients, antiseptics, pigments, dyes, colorants, humectants, propellants, waterproofing agents, film formers, vitamins as well as other classes of materials whose presence may be cosmetically, pharmaceutically, medicinally or otherwise desirable. Common examples can be found in the CTFA International Cosmetic Ingredient Dictionary 4 th Edition, The Cosmetic, Toiletry, and Fragrance Association, Inc., Washington, D.C., 1991, the contents of which are incorporated herein. The whitening compositions may also be useful in makeup products.

The compositions of the present invention may also comprise additional useful active ingredients which include, but are not limited to other known whitening agents, such as for example, tyrosinase inhibitors such as, for example, kojic acid, antioxidants, antimicrobials, analgesics, anesthetics, anti-acne agents, antidermatitis agents, antipruritic agents, antiinflammatory agents, antihyperkeratolytic agents, anti-dry skin agents, antiperspirants, antipsoriatic agents, antiseborrheic agents, antiaging agents, antiwrinkle agents, self-tanning agents, wound-healing agents, corticosteroids, or hormones. The incorporation of the active in the formulation is determined by its solubility and/or stability in combination with the Ascomycete derived melanin-degrading enzyme of the present invention. The selection of the mode of delivery for additional active ingredients, however, is limited to the mode of delivery chosen for the whitening compositions.

The invention is further illustrated by the following non-limiting example.

EXAMPLES

I. Preparation of a Whitening Composition

| Material | Weight % |
|---|---|
| Phase I | |
| Stearic Add | 2.0 |
| Glyceryl Stearate | 2.0 |
| Mineral Oil | 12.0 |
| Petrolatum | 4.0 |
| Parabens | 0.4 |
| Phase II | |
| Water | 35.0 |
| Propylene Glycol | 5.0 |

| Material | Weight % |
| --- | --- |
| Trisodium EDTA | 0.2 |
| Parabens | 0.4 |
| Phase III | |
| Water | 38.0 |
| Aspergillus fumigatus enzyme extract | 1.0 |

Phase I ingredients and Phase II ingredients are combined in separate vessels and each combination is heated with stirring to 70° C. The combined Phase I ingredients are then added with stirring to the combined Phase II ingredients. The mixture is allowed to cool to 30° C. while stirring. The Phase III ingredients are combined and added to Phase I and II ingredients to form a final emulsion. The *Aspergillus fumigatus* enzyme extract is NRRL 6463 obtained from ATCC.

II. Whitening Action of *Aspergillus fumigatus* Enzyme Extract

A comparative study is done to determine the efficacy of an *Aspergillus fumigatus* enzyme extract in comparison with the efficacy of a known tyrosinase inhibitor, kojic acid. Three samples are prepared. The first sample contains the base formula for a lotion without any whitening agent added to the formula. The second sample is the same base formula with 2% kojic acid added to the formula. Finally, the third sample contains the whitening agent of the present invention of 1% *Aspergillus fumigatus* enzyme extract in the base formula, as similarly described in Example I above.

Ten volunteer panelists participate in this study. To qualify for the study, the panelist is required to be in normal health with no evidence of acute or chronic disease including dermatologic problems. The panelists are female, ranging in age from 18 to 45, and having skin type I-II. In addition, the panelists do not exhibit sunburn effects, rashes, scratches, or burn marks as these conditions might interfere with the analysis of the test results. Pregnant or lactating females are also excluded. Upon examination at the site of testing, the participating panelists are examined to determine that they are devoid of excessive warts, nevi, moles, sunburn, suntan, scars or active dermal lesions. Finally, the panelists do not use systemic or topical retinoids, antihistamines or similar agents during the course of the study and two weeks prior to the commencement of the study.

Four distinct areas of about 4 cm² are marked on the backs of each of the panelists. Three of the four areas correspond to the lotion without a whitening agent, lotion with 2% kojic acid, and the lotion with 1% *Aspergillus fumigatus* enzyme extract of the present invention. The fourth area serves as the untreated irradiated control. Each panelist receives twice the MED of UV-B on each site area. The sites are radiated with a Xenon Arc Solar Simulator (150 Watt) with filters (mm UG-5) to expose the skin to UV-B and UV-A radiation. Tanning is observed for 7 days after irradiation at which point baseline color measurements are made using a Minolta Chromameter which measures the difference in reflectance of the skin, L. The change in the value of the difference in reflectance is, $\Delta L^*$. The delta values are measured against a baseline skin color value measured on day 7. The test materials are applied to the respective sites at a rate of 2 mg/cm² after the chromameter measurement on day 7, and are allowed to dry for 10 minutes. Product treatments are continued once a day for 7 days (i.e., day 8 to day 14 of the test). Chromameter readings are obtained on day 9, day 12, and day 14 after irradiation. An increase in skin tanning is observed with the chromameter for about 9 days after irradiation.

Results are shown in FIGS. 1 and 2. In FIG. 1, the skin whitening effect of 1% *Aspergillus fumigatus* enzyme extract ("Aspergillus extract") shows that it is greater than 2% kojic acid, twice the amount of the enzyme extract. The comparison is measured in terms of reflectance, ($\Delta L^*$), and it indicates that the enzyme extract containing compositions of the present invention have a lower reflectance and therefore, greater whitening effect. Since skin tanning continued to increase until about day 9, data for days 12 and 14 are normalized against the average data for day 9. In FIG. 2, comparison of the three formulas in terms of the percent skin color reduction, between day 9 and day 14 is provided. The data in FIG. 2 shows that the composition of the present invention, containing half the amount of enzyme extract (1%) than the amount of kojic acid (2%), produces a greater reduction in color of the skin.

III. Whitening Action of *Saccharomyces cerevisiae* Enzyme Extract

Yeast is grown in 10% colloidal mineral in YM broth for 3 days. The grown yeast is sonicated in a water bath sonicator for about 30 minutes and filtered. Melanin is prepared by incubating 1 mg/ml, cold dl 3,4-dihydroxy phenylalanine (DOPA) with 250 $\mu$Ci of $C^{14}$ DOPA in PBS. The polymerization is started with 10 units/ml of mushroom tyrosinase and is allowed to proceed until it is dark and insoluble melanin pigment is observed. The melanin thus prepared is stored at 4° C.

Insoluble radiolabeled $C^{14}$-melanin is prepared from synthetic melanin by repeated centrifugation or about 1.0 ml at about 10,000 rpm for about 15 minutes. Centrifugation is repeated three times. Each time, about 1.0 ml of melanin is added and the supernatant is discarded. Pooled insoluble melanin is resuspended in about 100 $\mu$ls of PBS and used as substrate. The reaction mixture consists of 10 $\mu$ls of radiolabeled melanin, 70 $\mu$ls of PBS, and intervals of about 0, 25, 50, and 100 $\mu$ls of cell homogenate of fraction (yeast extract). The reaction mixture is incubated for about one week at 37° C. while it is shaken. The reactions are stopped by the addition of scintillation fluid and the melanin count is taken. The treatments are done in triplicate. A decrease in total melanin count after one week of incubation is observed. It is found that the yeast extract decreases the amount of radiolabeled 24 percent, 29 percent and 54 percent for the intervals 25, 50 and 100 $\mu$ls of crude yeast extract, respectively.

IV. Whitening Action of *Saccharomyces cerevisiae* Enzyme Extract

| Material | Weight % |
| --- | --- |
| Phase I | |
| Stearic Acid | 2.0 |
| Glyceryl Stearate | 2.0 |
| Mineral oil | 10.0 |
| Petrolatum | 2.0 |
| Parabens | 0.4 |
| Phase II | |
| Water | 40.0 |
| Triethanolamine | 1.0 |
| Trisodium EDTA | 0.2 |
| Propylene Glycol | 5.0 |
| Parabens | 0.4 |

-continued

| Material | Weight % |
|---|---|
| Phase III | |
| Water | 36.0 |
| Saccharomyces cerevisiae yeast extract | 1.0 |

A study is done to determine the efficacy of a *Saccharomyces cerevisiae* enzyme extract in comparison with the efficacy of a known tyrosinase inhibitor, kojic acid. A samples of the yeast enzyme extract and 2% kojic acid are prepared separately in a triethanolamine (TEA) stearate base. The first sample contains the base formula for a lotion 1% *Saccharomyces cerevisiae* enzyme extract added to the formula. The second sample is the same base with 2% kojic acid added to the formula.

Seven volunteer panelists participate in this study. To qualify for the study, the panelist is required to be in normal health with no evidence of acute or chronic disease including dermatologic problems. The panelists are female, ranging in age from 18 to 45, and having skin type I-II. In addition, the panelists do not exhibit sunburn effects, rashes, scratches, or burn marks as these conditions might interfere with the analysis of the test results. Pregnant or lactating females are also excluded. The panelists appear to be in normal health and do not have signs of acute or chronic disease, including dermatologic problems. Upon examination at the site of testing, the participating panelists are examined to determine that they are devoid of excessive warts, nevi, moles, sunburn, suntan, scars or active dermal lesions. Finally, the panelists do not use systemic or topical retinoids, antihistamines or similar agents during the course of the study and two weeks prior to the commencement of the study.

Distinct areas of about 4 cm$^2$ are marked on the backs of each of the panelists each for applying the two samples, i.e., lotion with 2% kojic acid, and the lotion with 1% *Saccharomyces cerevisiae* enzyme extract of the present invention. An additional area is marked as the untreated irradiated control. Each panelist receives twice the MED of UV-B on each site area. The sites are radiated with a Xenon Arc Solar Simulator (150 Watt) with filters (mm UG-5) to expose the skin to UV-B and UV-A radiation. Tanning is observed for 5 days after irradiation at which point baseline color measurements are made using a Minolta Chromameter which measures the difference in reflectance of the skin, L. The change in the value of the difference in reflectance is, $\Delta L^*$. The delta values are measured against a baseline skin color value measured on day 7. The test materials are applied to the respective sites at a rate of 2 mg/cm$^2$ after the chromameter measurement on day 7, and are allowed to dry for 10 minutes. Product treatments are continued once a day for 7 days (i.e., day 8 to day 14 of the test). Chromameter readings are obtained on day 9, day 12, and day 14 after irradiation. An increase in skin tanning is observed with the chromameter for about 9 days after irradiation. Results indicate that the samples containing the yeast enzyme extract (1%) produces a reduction in color of the skin.

What we claim is:

1. A topical cosmetic or pharmaceutical composition for application to the skin comprising a whitening effective amount of at Aspergillus-derived melanin-degrading enzyme extract and a cosmetic or pharmaceutical carrier.

2. The composition of claim 1 wherein said Aspergillus-derived enzyme extract is the species *Aspergillus fumigatus*.

3. The composition of claim 1 wherein said enzyme is a purified extract solution.

4. The composition of claim 1 wherein said enzyme extract is present in an amount of about 0.05 to 5.00 percent by weight.

5. The composition of claim 2 further comprising a sunscreen.

6. A method of whitening the skin comprising topically applying a composition comprising an Aspergillus-derived melanin-degrading enzyme extract to the skin.

7. The method of claim 6 wherein the Aspergillus is the species *Aspergillus fumigatus*.

8. The method of claim 6 wherein the enzyme extract is present in an amount of about 0.05 to about 5.00 percent by weight of the composition.

9. A method of degrading melanin in the skin which comprises applying to the skin the composition of claim 3.

10. A method of inhibiting a UV-B induced tan comprising topically applying a composition comprising a whitening effective amount of an Ascomycete melanin-degrading enzyme extract derived from the genus Aspergillus.

11. The method of claim 9 wherein the whitening effective amount is about 0.05 to about 5.00 percent by weight of the composition and the enzyme extract is derived from the species *Aspergillus fumigatus*.

* * * * *